(12) United States Patent  (10) Patent No.: US 8,784,487 B2
Blom et al.  (45) Date of Patent: Jul. 22, 2014

(54) CATHETER FOR INSERTING A VOICE PROSTHESIS

(75) Inventors: Eric D. Blom, Carmel, IN (US); Bradley T. Kracht, Westfield, IN (US); Eric Gerard Johnson, New Albany, IN (US); Bryan E. Kostelac, Camby, IN (US)

(73) Assignee: Helix Medical, LLC, Carpinteria, CA (US)

( * ) Notice: Subject to any disclaimer, the term of this patent is extended or adjusted under 35 U.S.C. 154(b) by 215 days.

(21) Appl. No.: 13/446,657

(22) Filed: Apr. 13, 2012

(65) Prior Publication Data

US 2013/0274876 A1   Oct. 17, 2013

(51) Int. Cl.
   *A61F 2/20*   (2006.01)
(52) U.S. Cl.
   USPC ............................................................ 623/9
(58) Field of Classification Search
   USPC .................................................. 623/14.11, 9
   See application file for complete search history.

(56) References Cited

U.S. PATENT DOCUMENTS

| | | | |
|---|---|---|---|
| 4,435,853 A | 3/1984 | Blom et al. | |
| 4,541,427 A | 9/1985 | Koss | |
| 4,826,481 A | 5/1989 | Sacks et al. | |
| 4,911,716 A | 3/1990 | Blom et al. | |
| 5,064,433 A | 11/1991 | Blom et al. | |
| 5,078,743 A | 1/1992 | Mikalov et al. | |
| 5,300,119 A | 4/1994 | Blom | |
| 5,314,470 A | 5/1994 | Persson | |
| 5,403,264 A | 4/1995 | Wohlers et al. | |
| 5,571,180 A | 11/1996 | Blom | |
| 5,919,231 A * | 7/1999 | Blom et al. | 623/9 |
| 5,935,165 A | 8/1999 | Schouwenburg | |
| 5,976,151 A | 11/1999 | Siegbahn | |
| 6,139,541 A | 10/2000 | Vanney et al. | |
| 6,159,243 A | 12/2000 | Schouwenburg | |
| 6,776,797 B1 * | 8/2004 | Blom et al. | 623/14.11 |
| 6,921,417 B2 | 7/2005 | Persson | |
| 7,059,327 B2 | 6/2006 | Worthington | |
| RE39,923 E * | 11/2007 | Blom | 623/9 |
| 7,909,868 B2 | 3/2011 | Blom | |
| 7,975,696 B2 | 7/2011 | Blom | |

(Continued)

FOREIGN PATENT DOCUMENTS

| | | |
|---|---|---|
| EP | 2110101 A2 | 10/2009 |
| EP | 2110152 A2 | 10/2009 |
| WO | 2005097001 A1 | 10/2005 |
| WO | 2013/089644 A1 | 6/2013 |

OTHER PUBLICATIONS

Australian Office Action dated Aug. 30, 2013.

*Primary Examiner* — Suzette J Gherbi
(74) *Attorney, Agent, or Firm* — Daniel J. Sepanik, Esq.; Harness, Dickey & Pierce, P.L.C.

(57) ABSTRACT

A catheter, voice prosthesis assembly, and delivery method include an elongated flexible body having a hollow voice prosthesis tubing disposed on a first end of the elongated flexible body. A voice prosthesis is received in the hollow voice prosthesis tubing. The voice prosthesis having an interior esophageal flange at a first end and an exterior tracheal flange at a second end, with the voice prosthesis being received in the hollow voice prosthesis tubing with the interior esophageal flange being folded within the hollow voice prosthesis tubing and the exterior tracheal flange being disposed exterior to the hollow voice prosthesis tubing.

18 Claims, 6 Drawing Sheets

(56) References Cited

U.S. PATENT DOCUMENTS

| | | |
|---|---|---|
| 2003/0212349 A1 | 11/2003 | Meier |
| 2004/0204759 A1* | 10/2004 | Blom et al. ................ 623/9 |
| 2005/0154412 A1 | 7/2005 | Krueger et al. |
| 2006/0085005 A1 | 4/2006 | Kenealy et al. |
| 2009/0036876 A1 | 2/2009 | Tran |
| 2009/0043386 A1 | 2/2009 | Persson |
| 2009/0062927 A1* | 3/2009 | Marten et al. ............. 623/23.65 |
| 2009/0171280 A1* | 7/2009 | Samuel et al. ............. 604/99.04 |
| 2009/0318875 A1 | 12/2009 | Friedman |
| 2013/0274634 A1* | 10/2013 | Blom et al. ................... 600/593 |

* cited by examiner

CATHETER FOR INSERTING A VOICE PROSTHESIS

FIELD

The present disclosure relates to a catheter and delivery method for inserting a voice prosthesis.

BACKGROUND

This section provides background information related to the present disclosure which is not necessarily prior art.

A voice prosthesis is a one-way valve placed into a puncture between the trachea and the esophagus of a user who cannot speak following total laryngectomy, or surgical removal of the larynx (voice box). The voice prosthesis allows air to flow from the lungs through the trachea and into the esophagus to enable tracheoesophageal voice/speech. Flanges at both ends of the voice prosthesis retain the prosthesis in the tracheoesophageal puncture. Prior to voice prosthesis insertion, a dilator has been used to prevent the puncture from closing, eliminate leakage of the esophageal content and to dilate the puncture prior to initial insertion and later re-insertion of the voice prosthesis. An exemplary known dilator device is a BLOM-SINGER® tracheoesophageal puncture dilator available from InHealth Technologies, a division of Helix Medical, LLC.

After removal of a surgical catheter or voice prosthesis, the dilator maintains the open fistula. Once inserted, the dilator is taped in place on the neck. This device is then removed after several minutes of dilation. Once the fistula is dilated, it needs to be sized. A voice prosthesis sizer, such as the BLOM-SINGER® voice prosthesis sizer available from InHealth Technologies, a division of Helix Medical, LLC, is placed on an inserter and the device is inserted into the fistula. The sizer is gently withdrawn until resistance is detected indicating that the esophageal collar is seated against the interior wall of the esophagus. The size is then read at the mark closest to the puncture entrance. After sizing, a voice prosthesis is then inserted into the puncture for voicing.

U.S. Pat. No. 7,975,696, assigned to an assignee of the present application, is directed to a voice prosthesis dilator and sizer device that combines the functions of the separate voice prosthesis dilator and the sizer into a single device in order to provide a dilating and sizing function that is gentler on the fistula in that only one insertion is needed rather than two. The voice prosthesis dilator and sizer device is used by a clinician for replacing an existing voice prosthesis in an existing tracheoesophageal puncture.

It is desirable to provide a catheter device and delivery method that is intended for use in surgical procedures wherein the primary (during total laryngectomy) or secondary tracheoesophageal puncture is formed, and wherein the catheter can be used for dilation, selection of proper length voice prosthesis, and placement of a voice prosthesis during the surgical procedure while a patient is typically sedated.

SUMMARY

This section provides a general summary of the disclosure, and is not a comprehensive disclosure of its full scope or all of its features.

The present disclosure provides a catheter, voice prosthesis assembly, and delivery method including an elongated flexible body having a hollow voice prosthesis tubing disposed on a first end of the elongated flexible body. A voice prosthesis is received in the hollow voice prosthesis tubing. The voice prosthesis having an interior esophageal flange at a first end and an exterior tracheal flange at a second end, with the voice prosthesis being received in the hollow voice prosthesis tubing with the interior esophageal flange being folded within the hollow voice prosthesis tubing and the exterior tracheal flange being disposed exterior to the hollow voice prosthesis tubing.

A method of inserting a voice prosthesis into a tracheoesophageal puncture of a patient is provided and includes the steps of inserting a voice prosthesis into a hollow voice prosthesis tubing on a first end of an elongated catheter so that an interior esophageal flange of the voice prosthesis is folded within the hollow voice prosthesis tubing and an exterior tracheal flange of the voice prosthesis is disposed exterior to the hollow voice prosthesis tubing. A second end of the catheter is inserted into the tracheoesophageal puncture of the patient and is fed upward through the esophagus and out of the patient's mouth. The catheter is pulled out through the patient's mouth until the tracheal flange engages an outer surface of the puncture and the catheter is pulled so as to cause the voice prosthesis to disengage from the hollow voice prosthesis tubing, allowing the interior esophageal flange to be deployed on the esophageal side of the puncture.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Figure 1:
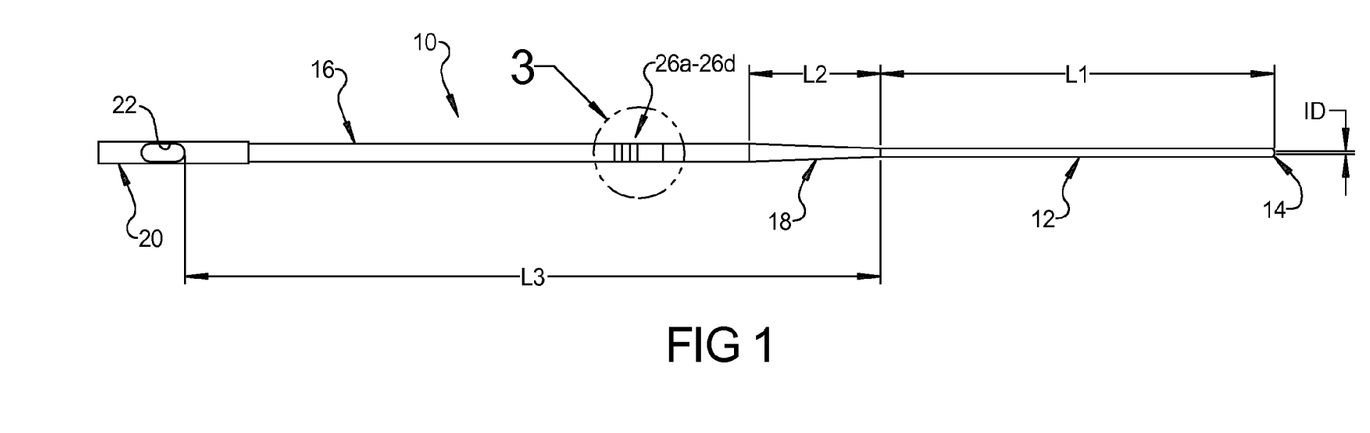
FIG. 1 is a side plan view of the catheter for inserting a voice prosthesis according to the principles of the present disclosure.
Figure 2:
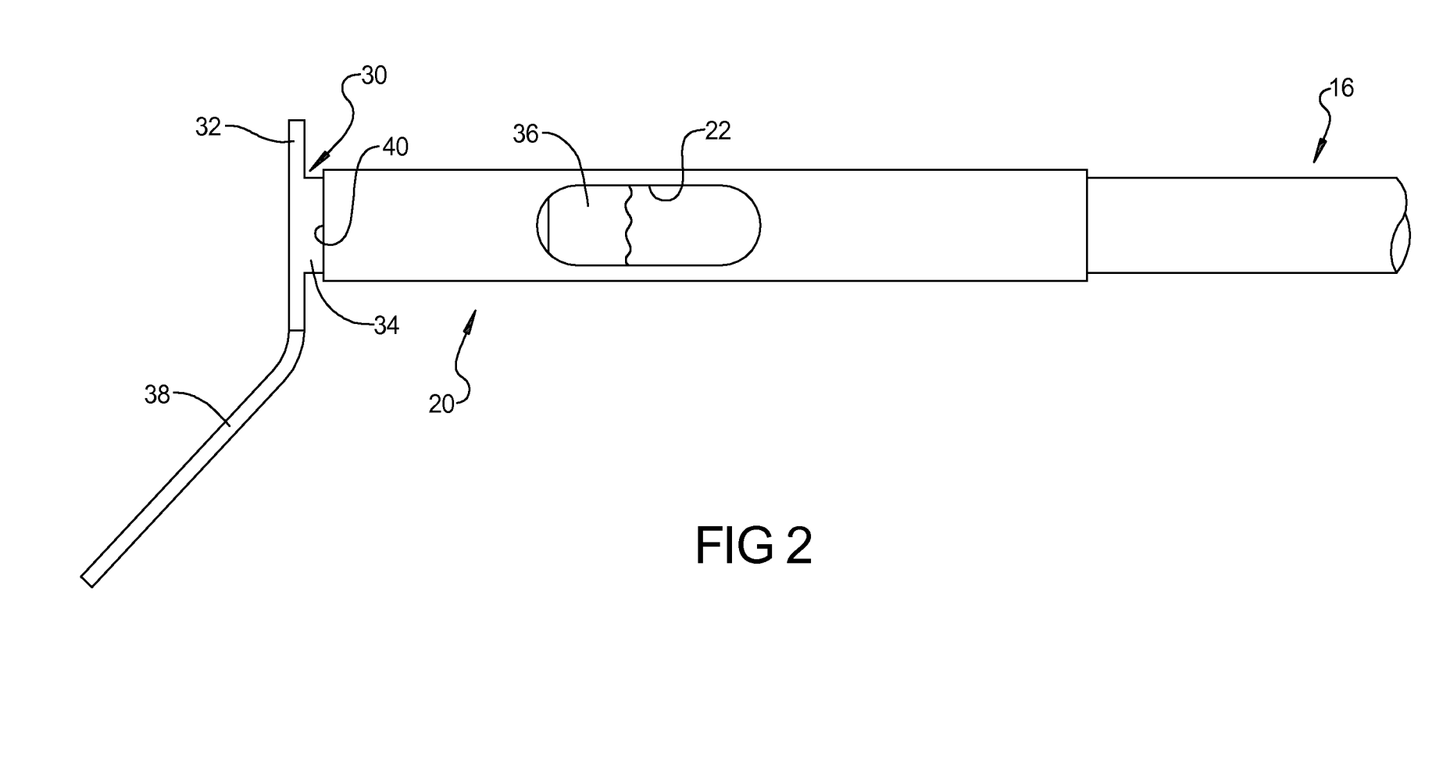
FIG. 2 is an enlarged view of a first end of the catheter supporting a voice prosthesis therein according to the principles of the present disclosure.
Figure 3:
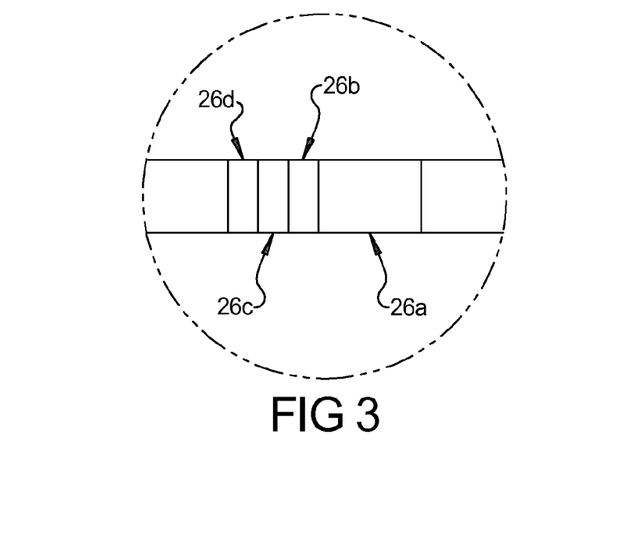
FIG. 3 is an enlarged detailed view of the measuring indicia provided on the catheter according to the principles of the present disclosure.

With reference to FIGS. 1-3, a catheter 10 for inserting a voice prosthesis according to the principles of the present disclosure, will now be described. The catheter 10 includes a distal portion 12 that can include a tubing having a rounded tip 14 and an interior aperture extending therethrough. A proximal portion 16 is connected to the distal portion 12 and can also include a tubing having an aperture extending therethrough. The proximal portion 16 can also include a tapered section 18 that connects to the distal portion 12.

The proximal and distal portions 16, 12 can be attached to one another by thermal, adhesive, or solvent bonding, for example, and can each include interior diameter (ID) of between 0.03 and 0.045 inches, and more particularly, approximately 0.038 inches. The distal portion 12 can have a length L1 of between 12 and 36 inches, and more preferably, 24 inches. The tapered section 18 of the proximal portion 16 can have a length L2 of between one and three inches, and more preferably, 1.5 inches. The entire length of the proximal portion 16 can be between five and twelve inches, and more preferably eight inches.

Proximal portion 16 of the catheter 10 is received in a tubular-shaped voice prosthesis holder 20 that can have an inner diameter approximately equal to the outer diameter of the proximal portion 16 wherein the proximal portion is received within the voice prosthesis holder 20 and can be thermally, adhesively, or solvent bonded thereto. By way of example, the outer diameter of the proximal portion and the inner diameter of the voice prosthesis holder 20 can be sized for a 16 French or 20 French voice prosthesis.

The voice prosthesis holder 20 can include an opening 22 in its side wall that can be in the form of an aperture through which a voice prosthesis can be loaded within the tubular-shaped voice prosthesis holder 20. The aperture 22 can be oval in shape and have a length of approximately 0.5 inches and a width of approximately 0.18 inches, although it should be understood that other dimensions and geometries could be used. The overall length of the tubular-shaped voice prosthesis holder 20 can be between one and three inches, and more preferably, approximately 1.75 inches. The voice prosthesis holder 20 can be lubricated on the inside diameter of the tube to facilitate insertion of a voice prosthesis. The lubricant can be applied to the inside diameter at time of manufacturing and can include a silicone based lubricant. The lubricant will reduce the coefficient of friction to $0.04 \leq \mu_k \leq 1$ of the tube between the voice prosthesis. The lubricant can be permanent or semi-permanent and maintains its lubricity until needed. More preferably, the coefficient of friction must not be too great as to interfere with loading and placement of the voice prosthesis. The proximal portion 16 of the catheter can be inserted inside of the voice prosthesis holder by a distance that can be 0.75 inches.

Each of the distal portion 12, proximal portion 16, and voice prosthesis holder 20 can be made from a polymer such as PEBAX® wherein it is noted that the distal portion 12 can have a hardness of 72 durometer while the proximal portion 16 can have a hardness of 40 durometer in order to provide the catheter 10 with an appropriate stiffness for manipulation within a patient during the surgical procedure.

The tapered portion 18 of the catheter 10 can be utilized for dilating the puncture (P) provided between the trachea (T) and the esophagus (E) of a patient in order to prepare the puncture for receipt of a voice prosthesis device. Measuring indicia 26a-26d are provided on a selected area of the proximal portion 16 and can include color coded markings or other markings indicative of a length of the puncture between the walls of the trachea and the esophagus of a patient. According to one embodiment, the color coding of the rings 26a-26d can allow a surgeon to align the end of the wide band 26a with the interior wall of the puncture using a scope that is inserted into the esophagus, and then to visually observe the color of the ring 26b, 26c, or 26d that is exposed on the exterior side of the puncture in order to properly determine a length size of a voice prosthesis to be inserted into the puncture. Once the proper sizing is determined, the selected voice prosthesis device is installed into the voice prosthesis holder 20. As illustrated in FIG. 2, the voice prosthesis 30 includes an exterior tracheal flange 32 connected to a cylindrical body 34 that is received in the end of the voice prosthesis holder 20. An esophageal interior flange 36 is seen folded in an axial direction, pointing toward the distal portion 12, within the aperture 22 of the voice prosthesis holder 20.

The voice prosthesis 30 is inserted into the voice prosthesis holder 20 by inserting a strap 38 that extends from the tracheal flange 32 through the aperture 22 and out of the end of the voice prosthesis holder 20. As the strap 38 is pulled through the end of the voice prosthesis holder 20, the esophageal flange 36 of the prosthesis is folded and fed down and into the aperture 22. The tracheal flange 32 is pulled through the opening 22 and out the end 40 of the voice prosthesis holder 20. Once the strap 38 and tracheal flange 32 is deployed out the end of the voice prosthesis holder 20, the esophageal flange 36 should be fully drawn into the voice prosthesis holder 20, as can be seen in the opening 22 in the illustration of FIG. 2. It is noted that the distance from the end 40 from the voice prosthesis holder to the beginning of the aperture 22 would determine how much of the esophageal flange 36 would be exposed in the opening 22.

It is noted that, as well known in the art, the voice prosthesis device 30 would include an internal valve V therein of any known type. It should be further noted that other methods of loading the voice prosthesis into the voice prosthesis holder 20 can also be utilized including other arrangements of slots or openings provided in the side of the voice prosthesis holder 20. Furthermore, insertion techniques that do not use openings, apertures, or slots in the sides of the voice prosthesis holder 20 could also be utilized, for example, using the method of folding and loading the esophageal flange of a voice prosthesis as described in the Blom-Singer® Gel Cap Insertion System, as described in prior art U.S. Pat. No. RE39,923 (Blom), U.S. Pat. No. 5,571,180 (Blom), and U.S. Pat. No. 6,776,797 (Blom et al), which are herein incorporated by reference.

Figure 4:
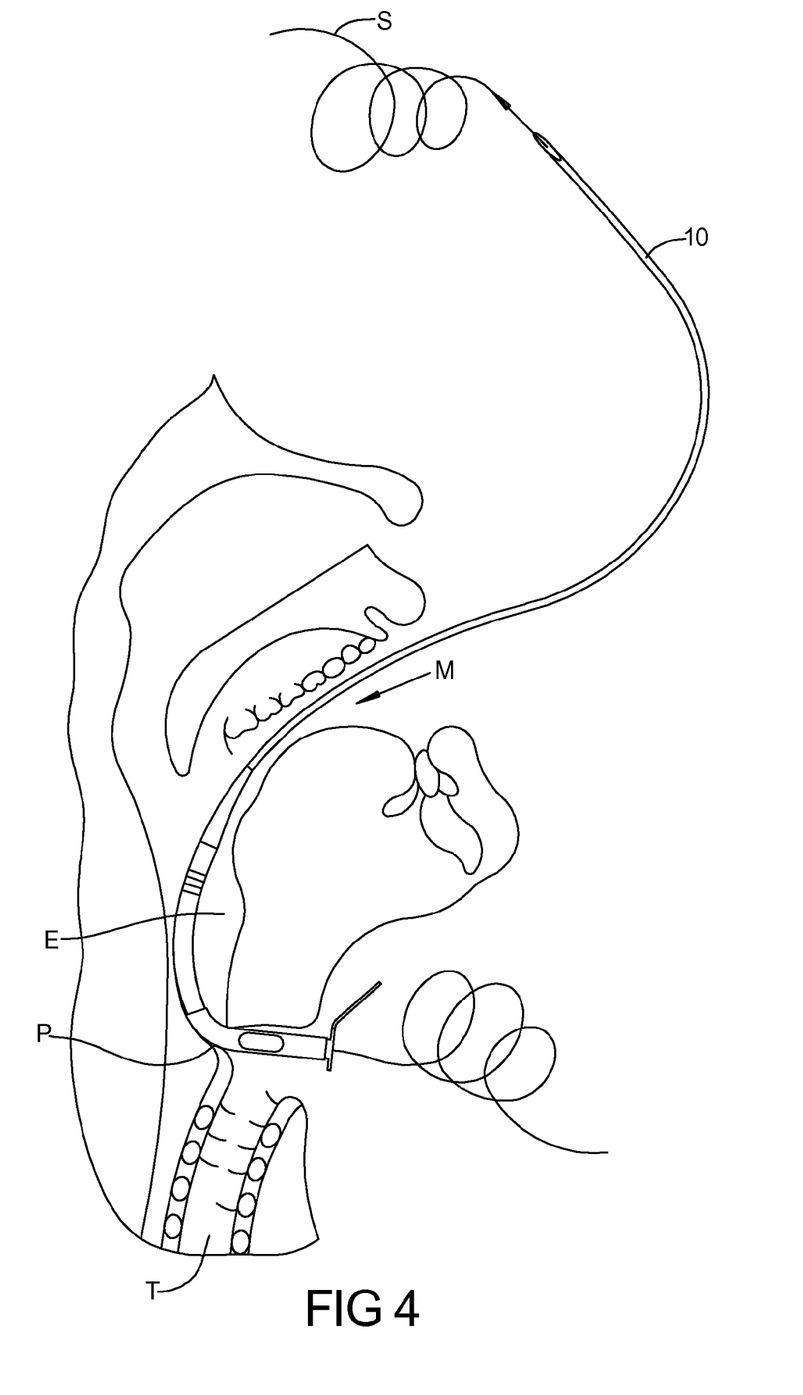
FIG. 4 is a schematic illustration of the insertion of the catheter through a puncture between the trachea and esophagus of a patient according to the principles of the present disclosure.

With reference to FIG. 4, during a surgical procedure, a puncture P is provided between the trachea T and esophagus E of the patient using known puncture techniques. A trocar and pharynx protector device may be utilized for creating the puncture. Optionally, as illustrated in FIG. 4, a stringer S, such as a cable or wire, can be inserted to extend through the patient's mouth and out through the puncture P using known techniques. The catheter 10 can be utilized by inserting the stringer S through the opening in the catheter, or the catheter can be used independently of a wire wherein a distal end 12 of the catheter 10 is inserted through the puncture P, through the esophagus E, and out of the patient's mouth M.

As the catheter 10 is pulled outward through the patient's mouth M, the tapered section 18 of the catheter 10 can be disposed within the puncture P in order to dilate the puncture for insertion of the prosthesis device 30. Once the puncture P is dilated, the measuring indicia 26a-26d can be utilized for measuring the length of the puncture P in order to determine an appropriate length sized voice prosthesis device 30. Once the measurement is taken by aligning the inner indicia 26a with the inner wall of the esophagus E and visually inspecting the indicia 26b-26d on the outside of the puncture P on the trachea side, the appropriately length sized voice prosthesis 30 can then be inserted into the voice prosthesis holder 20 in the manner as described above.

Figure 5:
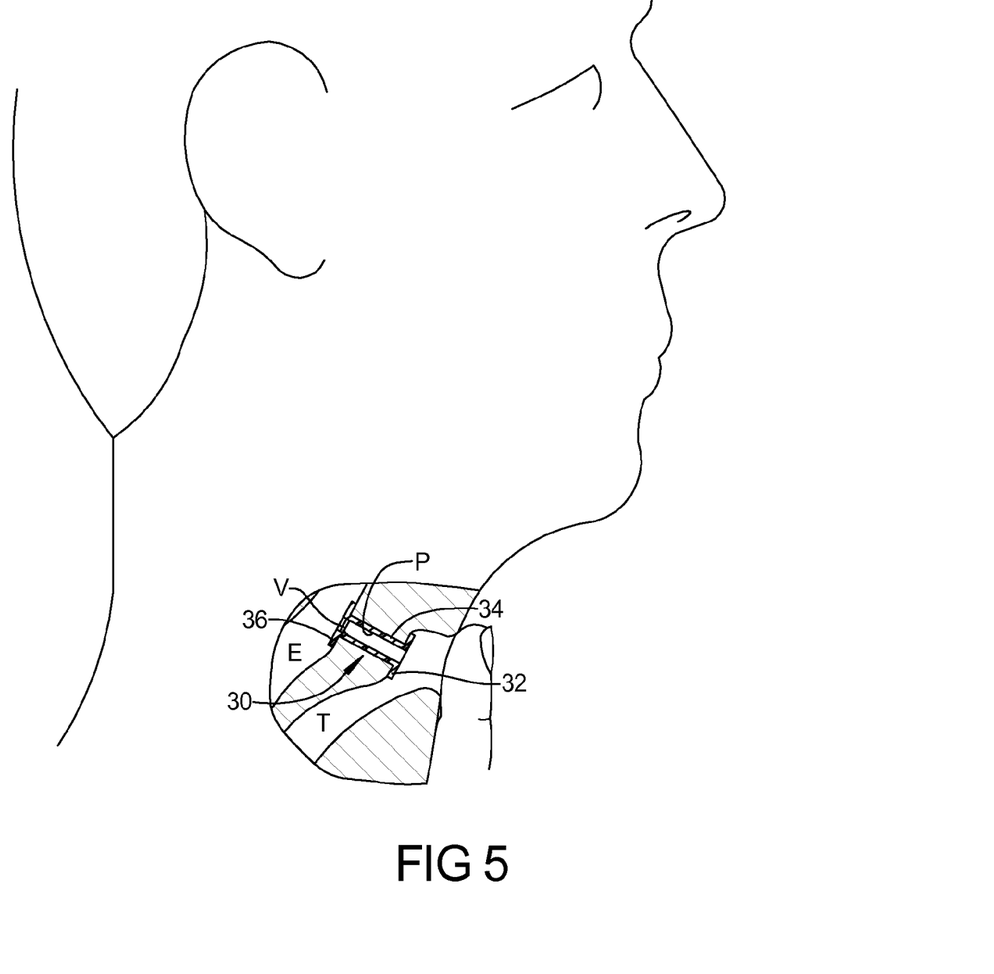
FIG. 5 is a schematic illustration of the placement of a voice prosthesis in a puncture between the trachea and esophagus of a patient.

The catheter 10 can then be further pulled through the patient's mouth M and the puncture P until the tracheal flange 32 of the voice prosthesis 30 is disposed against the tracheal wall of the puncture P. The strap 38 of the voice prosthesis 30 can then be held either manually by the user's hand or by an inserter stick, or other known device, while the catheter 10 is continued to be pulled out of engagement with the voice prosthesis 30 so that the esophageal flange 36 of the voice prosthesis device 30 is allowed to be deployed on the interior of the puncture P inside of the esophagus E. FIG. 5 illustrates a voice prosthesis device 30 properly installed in a puncture P of a patient disposed between the trachea T and esophagus E.

Figure 6:
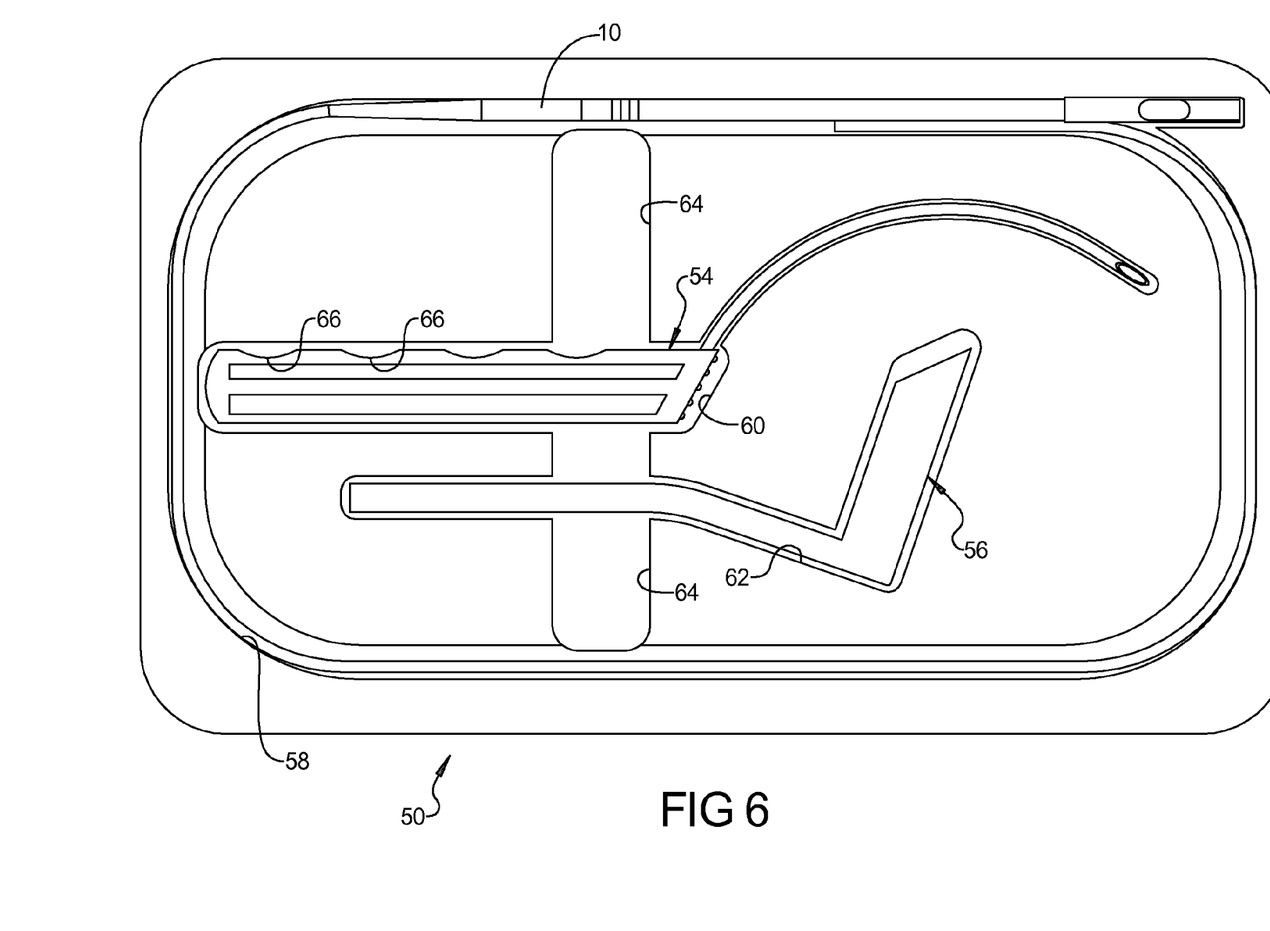
FIG. 6 is a top plan view of a tray for supporting and packaging the catheter as well as surgical instruments for use during surgical primary and secondary tracheoesophageal puncture and voice prosthesis placement according to the principles of the present disclosure.
Figure 7:
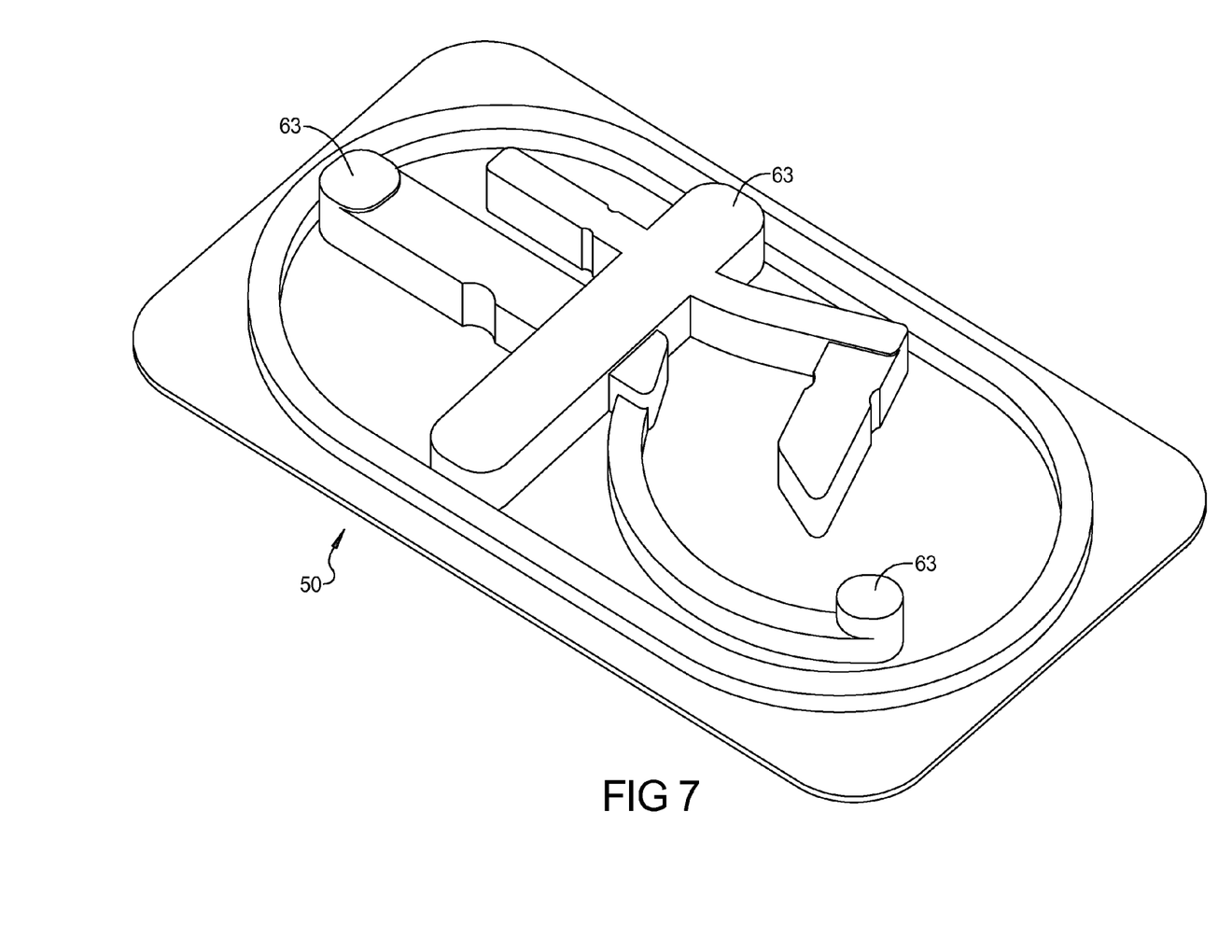
FIG. 7 is a bottom perspective view of the tray shown in FIG. 6.

With reference to FIGS. 6 and 7, a tray 50 is shown for holding the catheter 10 as well as surgical instruments such as a trocar 54 and pharynx protector 56 that are commonly utilized for creating the puncture P. The tray 50 can include a recessed channel 58 extending around the perimeter of the tray 50 for receiving the catheter 10 therein, as well as separate recesses 60, 62 for receiving each of the other surgical instruments 54, 56. The recesses 60, 62 can be provided with protruding retainer features 66 for holding the catheter and instruments in the tray. The tray can be made of various materials including plastics, and can maintain the catheter 10 and surgical instruments 54, 56 in a sterile condition during shipping and handling. As illustrated in FIG. 7, the back of the tray 50 can be provided with raised portions 63 to provide a stable support for the tray for use during surgery. The tray 50 can also provide recessed regions 64 along the recessed channels to allow a user's fingers to be inserted for easily removing the catheter 10 and surgical instruments 54, 56 therefrom. A lid can be placed over top of the tray with the catheter 10 and surgical instruments 54, 56 disposed therein to prevent them from being dislodged from the tray during shipping and handling. Furthermore, the lid can maintain the sterility of the various components.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A catheter and voice prosthesis assembly, comprising:
an elongated flexible body;
a hollow voice prosthesis tubing fixedly attached on a first end of said elongated flexible body; and
a voice prosthesis having an interior esophageal flange at a first end and an exterior tracheal flange at a second end, said voice prosthesis being received in said hollow voice prosthesis tubing with said interior esophageal flange being folded within the hollow voice prosthesis tubing and said exterior tracheal flange being disposed exterior to said hollow voice prosthesis tubing, wherein a wall of said hollow voice prosthesis tubing includes an opening in a side thereof for receiving said voice prosthesis therethrough.

2. The assembly according to claim 1, wherein said elongated flexible body is hollow with an aperture extending from said first end to a second end.

3. The assembly according to claim 1, wherein said hollow voice prosthesis tubing includes a lubricant with a coefficient of friction of $0.04 \leq \mu_k \leq 1$ between the voice prosthesis and the voice prosthesis holder.

4. The assembly according to claim 3, wherein said lubricant is a silicone based lubricant.

5. The assembly according to claim 3, wherein said opening in said hollow voice prosthesis tubing is an aperture.

6. The assembly according to claim 5, wherein said aperture in said hollow voice prosthesis tubing is generally oval.

7. A catheter and voice prosthesis assembly, comprising:
an elongated flexible body;

an a hollow voice prosthesis tubing fixedly attached on a first end of said elongated flexible body; and a voice prosthesis having an interior esophageal flange at a first end and an exterior tracheal flange at a second end, said voice prosthesis being received in said hollow voice prosthesis tubing with said interior esophageal flange within the hollow voice prosthesis tubing and said exterior tracheal flange being disposed exterior to said hollow voice prosthesis tubing, wherein said first end of said elongated flexible body has a first diameter and said second end of said elongated flexible body has a second diameter smaller than said first diameter and including a tapered section disposed between said first and second ends.

8. The assembly according to claim 7, wherein said elongated flexible body is at least 18 inches long.

9. The assembly according to claim 1, wherein said voice prosthesis includes a valve therein.

10. The assembly according to claim 1, wherein said voice prosthesis includes a strap extending from said exterior tracheal flange.

11. A catheter and voice prosthesis assembly, comprising:
an elongated flexible body;
a hollow voice prosthesis tubing fixedly attached on a first end of said elongated flexible body; and
a voice prosthesis having an interior esophageal flange at a first end and an exterior tracheal flange at a second end, said voice prosthesis being received in said hollow voice prosthesis tubing with said interior esophageal flange within the hollow voice prosthesis tubing and said exterior tracheal flange being disposed exterior to said hollow voice prosthesis tubing, wherein said elongated flexible body includes a plurality of measuring indicia thereon.

12. The assembly according to claim 11, wherein said measuring indicia includes a plurality of colored rings.

13. The assembly according to claim 11, wherein said measuring indicia includes a plurality of lines and/or a numbered scale.

14. The assembly according to claim 7, wherein said elongated flexible body includes a first tube at said first end having a first diameter and a second tube at said second end having a second diameter smaller than said first diameter and including a tapered portion connecting said first tube to said second tube.

15. The assembly according to claim 14, wherein said first tube, said tapered portion, and said second tube are bonded together.

16. The assembly according to claim 14, wherein said first tube has a lower hardness than said second tube.

17. The assembly according to claim 14, wherein said hollow voice prosthesis tubing is bonded to said elongated flexible body.

18. A catheter and voice prosthesis assembly, comprising:
a hollow elongated flexible body;
a hollow voice prosthesis tubing fixedly attached on a first end of said hollow elongated flexible body, said elongated flexible body and said voice prosthesis tubing each being hollow along an entire length thereof; and
a voice prosthesis having an interior esophageal flange at a first end and an exterior tracheal flange at a second end, said voice prosthesis being received in said hollow voice prosthesis tubing with said interior esophageal flange within the hollow voice prosthesis tubing and said exterior tracheal flange being disposed exterior to said hollow voice prosthesis tubing.

* * * * *

UNITED STATES PATENT AND TRADEMARK OFFICE
CERTIFICATE OF CORRECTION

PATENT NO. : 8,784,487 B2  
APPLICATION NO. : 13/446657  
DATED : July 22, 2014  
INVENTOR(S) : Eric D. Blom et al.

Page 1 of 1

It is certified that error appears in the above-identified patent and that said Letters Patent is hereby corrected as shown below:

In the Claims

At column 7, claim number 7, line number 1, before "a hollow" delete "an".

Signed and Sealed this  
Twentieth Day of January, 2015

Michelle K. Lee  
*Deputy Director of the United States Patent and Trademark Office*